US009687150B2

(12) United States Patent
Matarazzi et al.

(10) Patent No.: US 9,687,150 B2
(45) Date of Patent: Jun. 27, 2017

(54) HOUSEHOLD APPLIANCE INTERFACEABLE WITH A BIOMETRIC MONITORING SYSTEM

(71) Applicant: Indesit Company S.p.A., Fabriano (IT)

(72) Inventors: Filippo Matarazzi, Gualdo Tadino (IT); Carlo Filippo Ratti, Turin (IT); Marco Maria Pedrazzo, Cuneo (IT)

(73) Assignee: Whirpool EMEA SpA, Pero (MI) (IT)

( * ) Notice: Subject to any disclaimer, the term of this patent is extended or adjusted under 35 U.S.C. 154(b) by 0 days.

(21) Appl. No.: 14/677,100

(22) Filed: Apr. 2, 2015

(65) Prior Publication Data
US 2015/0282710 A1    Oct. 8, 2015

(30) Foreign Application Priority Data

Apr. 7, 2014   (IT) .............. TO2014A0290

(51) Int. Cl.
G09B 19/00 (2006.01)
G08C 19/22 (2006.01)
A61B 5/00 (2006.01)
F24C 7/08 (2006.01)
F25D 29/00 (2006.01)

(52) U.S. Cl.
CPC .............. *A61B 5/0024* (2013.01); *F24C 7/08* (2013.01); *F24C 7/085* (2013.01); *F25D 29/00* (2013.01); *F25D 2500/06* (2013.01); *F25D 2700/04* (2013.01); *F25D 2700/08* (2013.01)

(58) Field of Classification Search
CPC .................................................. A61B 5/0024
See application file for complete search history.

(56) References Cited

U.S. PATENT DOCUMENTS

2008/0001735 A1*  1/2008  Tran .................... G06F 19/3418
                                                                340/539.22
2013/0277353 A1* 10/2013  Joseph ................ H05B 1/0263
                                                                219/209
2014/0335490 A1* 11/2014  Baarman ................ A61B 5/002
                                                                434/236

FOREIGN PATENT DOCUMENTS

| CN | 202 993 741 U | 6/2013 |
| DE | 10 2009 026958 A1 | 12/2010 |
| EP | 1 918 643 A2 | 5/2008 |
| WO | WO 2007/035851 A2 | 3/2007 |
| WO | WO 2007/103958 A2 | 9/2007 |

OTHER PUBLICATIONS

International Search Report and Written Opinion mail date Aug. 22, 2014 for Italian Patent Application No. TO2014A000290 filed on Apr. 7, 2014 by Indesit Company S.p.A., 8 pages.

* cited by examiner

Primary Examiner — Joseph Feild
Assistant Examiner — John Mortell
(74) Attorney, Agent, or Firm — Cesari and McKenna, LLP

(57) ABSTRACT

The present invention relates to a household appliance (301) comprising means (302) for obtaining at least one piece of information about at least one food (303) with which the household appliance (301) is interacting, and further configured for transmitting (304) the piece of information to a biometric monitoring system (101, 601) of a user (201).

13 Claims, 4 Drawing Sheets

HOUSEHOLD APPLIANCE INTERFACEABLE WITH A BIOMETRIC MONITORING SYSTEM

CROSS REFERENCE TO RELATED APPLICATIONS

This application claims priority to Italian Application No. TO2014A000290, filed on Apr. 7, 2014, the contents of which are hereby incorporated by reference in its entirety.

TECHNICAL FIELD

The present invention relates to the field of "connected" household appliances, i.e. appliances adapted to interface to other devices and exchange information with them.

The invention particularly relates to a household appliance adapted to exchange information with a biometric monitoring system.

PRIOR ART

"Connected" household appliances are known which can interface to other devices and exchange information with them. The devices that such household appliances can interface to include, among others, smartphones, tablets and PC's in general; in such a case, interfacing essentially occurs in wireless mode, wherein information is transmitted through IP protocols, possibly over the Internet.

Such "connected" household appliances assist the user by providing a large amount of information that the user can exploit to his/her advantage.

However, the existing "connected" household appliances cannot provide adequate and effective assistance in certain situations.

In particular, the current "connected" household appliances are not able to deal with problems related to the user's psychophysical conditions, in particular deriving from the consumption of specific foods. It is known, in fact, that some foods can be a cause of discomfort or even health problems for some users, when ingested in certain quantities. On the other hand, some foods can contribute to improving the well-being of a user, in terms of both satisfaction and health.

Biometric monitoring systems exist which are adapted to monitor the instantaneous health conditions and vital signs of a user. However, the interaction with such biometric monitoring systems may be complex, in particular in relation to the consumption of foods.

OBJECTS AND SUMMARY OF THE INVENTION

It is the object of the present invention to overcome some of the problems of the prior art.

In particular, it is one object of the present invention to provide a household appliance that allows obtaining information useful for monitoring the user's psychophysical conditions.

It is another object of the present invention to provide a household appliance that simplifies the interaction between the user and biometric monitoring systems.

It is a further object of the invention to provide a household appliance which is an effective tool for evaluating problems related to the consumption of certain foods.

It is yet another object of the present invention to provide a household appliance that allows better exploitation, to the user's advantage, of the various information that can be transmitted in a "connected" environment.

These and other objects of the present invention are achieved through a household appliance incorporating the features set out in the appended claims, which are intended to be an integral part of the present description.

One idea at the basis of the present invention is to provide a household appliance which comprises means for obtaining at least one piece of information about at least one food with which said household appliance is interacting, and which is further configured for transmitting said at least one piece of information to a biometric monitoring system of a user.

It is thus possible to obtain from the household appliance information about foods, useful for monitoring the user's psychophysical conditions, in particular circumstances, by means of a biometric monitoring system.

Advantageously, the interaction between the user and the biometric monitoring system is automatically improved by the intervention of the household appliance, which autonomously transmits important information about the foods consumed by the user, such as food typology and/or food preparation typology.

In this manner, the household appliance becomes an effective tool for evaluating any problems related to the consumption of certain foods prepared by the user according to particular preparation cycles, whose biometric parameters are constantly monitored.

The household appliance according to the present invention, therefore, allows better exploitation, to the user's advantage, of the information about the foods.

Other particular and advantageous aspects of the present invention will be set out in the appended claims, which are an integral part of the present description.

Further objects and advantages of the present invention will become more apparent from the following detailed description and from the annexed drawings.

BRIEF DESCRIPTION OF THE DRAWINGS

Some preferred and advantageous embodiments will now be described by way of non-limiting example with reference to the annexed drawings, wherein.

The drawings show different aspects and embodiments of the present invention and, where appropriate, similar struc-

DETAILED DESCRIPTION OF THE INVENTION

Figure 1:
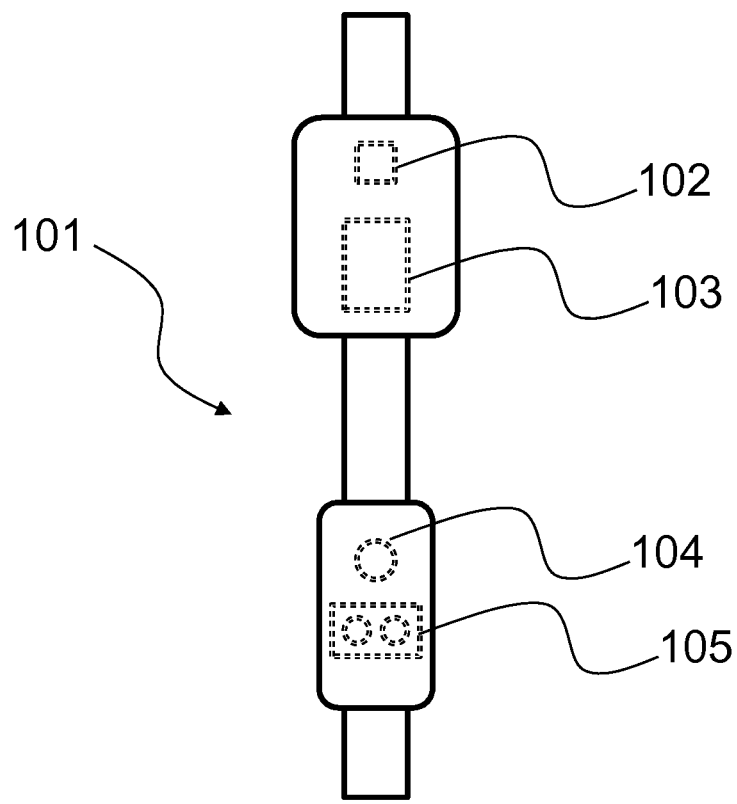
FIG. 1 shows a device of a biometric monitoring system, wearable by a user.

FIG. 1 illustrates a preferred embodiment of a biometric monitoring device, i.e. a bracelet 101 wearable by a user. The bracelet 101 comprises a plurality of sensors for monitoring at least one vital parameter of the user in real time; in particular, the bracelet 101 is adapted to monitor the user's physiological activity and mood changes.

The bracelet 101 preferably comprises a 3-axis accelerometer 102, a photoplethysmograph 103, a thermometer 104 and a sensor 105 comprising a plurality of electrodes adapted to measure the user's electrodermal activity.

The accelerometer 102 measures the acceleration perceived by the user. In principle, an accelerometer behaves like a mass mounted on a damped spring. When the accelerometer experiences an acceleration, the mass will move at a certain speed relative to the frame whereto the spring is secured. The displacement variation is then measured in order to obtain the acceleration. The accelerometer 102 is therefore used for measuring the user's activity and motion.

The photoplethysmograph (PPG) 103 takes a volumetric measurement on an organ through optical means. This measurement is obtained by using a pulse oximeter, which illuminates the skin by means of a light beam and measures the light absorption variations. A pulse oximeter measures blood perfusion to the derma and in the subcutaneous tissue of the skin. The volume variation caused by the blood pressure pulse is detected by illuminating the skin with light emitted by a LED diode, and then by measuring the quantity of light transmitted or reflected to a detector photodiode. The photoplethysmograph 103 is thus adapted to measure the heart beat and the heart beat variation, and to estimate a metabolic equivalent of task (MET) and, in general, an individual's stress conditions.

The thermometer 104 simply measures the temperatures of the user's skin in contact with the sensor, in order to estimate the global body temperature.

The electrodermal activity sensor 105 takes a measurement of the electric conductivity of the user's skin, which varies according to skin humidity caused by sweat. Sweating is controlled by the sympathetic nervous system; therefore, cutaneous conductance can be used as an indicator of psychological or physiological arousal. Therefore, if the sympathetic branch of the autonomic nervous system is much aroused, the sudorific activity of the glands will increase, resulting in increased cutaneous conductance. The sensor 105 can thus provide an estimation of the user's emotional responses.

Figure 2:
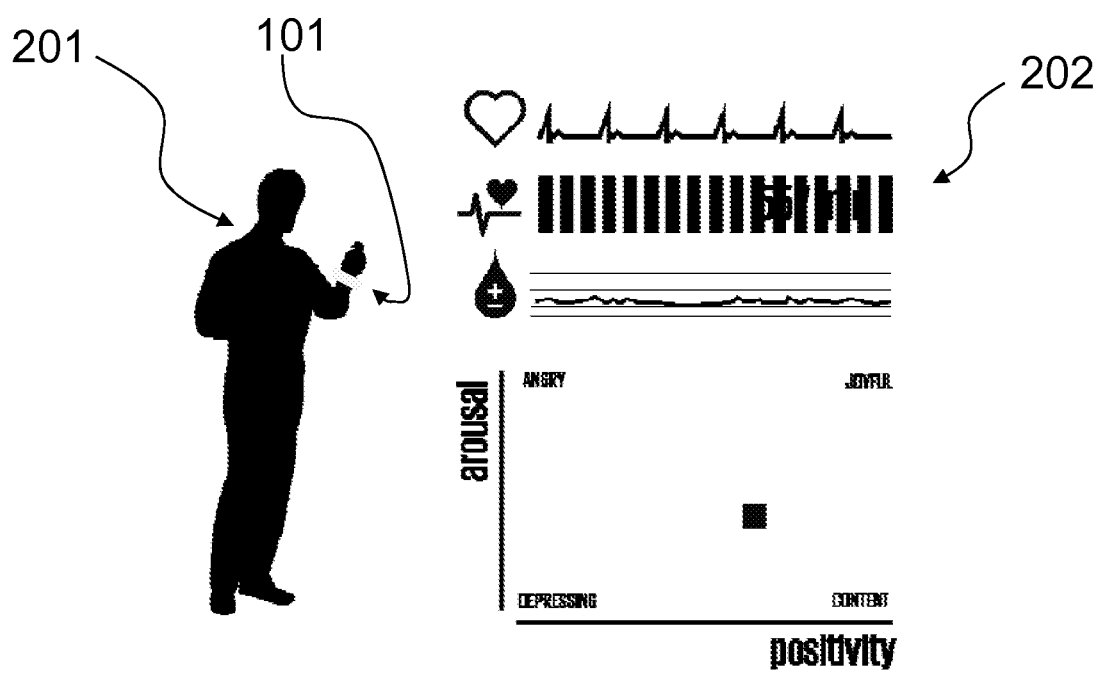
FIG. 2 shows the operation of the device of FIG. 1, worn by a user.

FIG. 2 illustrates the operation of the bracelet 101 when worn by a user 201. The user 201 is presented with several information about his/her vital and biometric parameters in various ways, e.g. through a displayable screen 202. In particular, the information that is preferably presented is about: heart rate, heart rate variation (HRV), pressure, electrodermal activity (cutaneous conductance), arousal, positivity, agitation, activity, movements.

Figure 3:
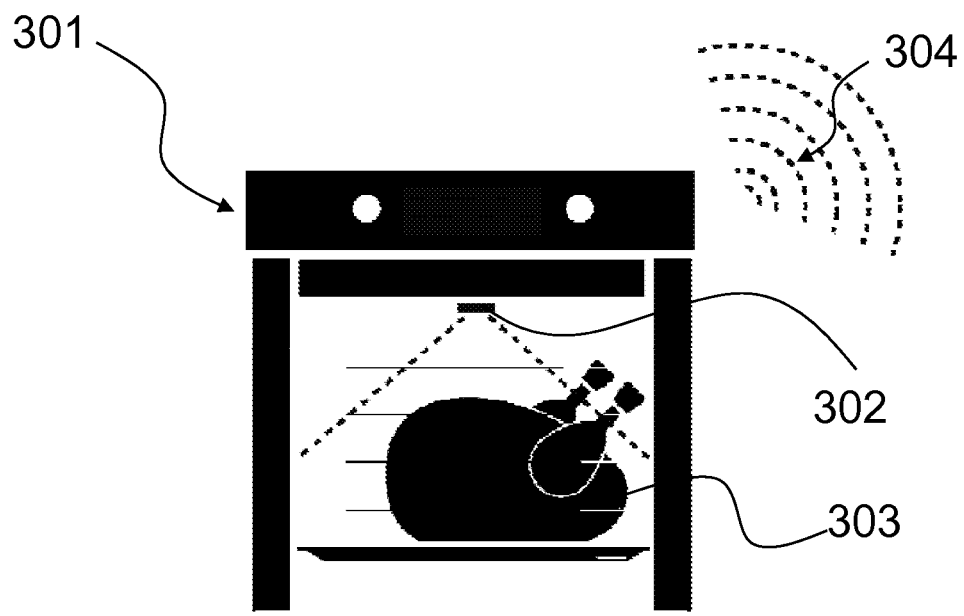
FIG. 3 shows the operation of a household appliance according to the present invention.

FIG. 3 illustrates a household appliance according to the present invention, which in the preferred embodiment is an oven 301.

The oven 301 comprises means 302 configured for receiving at least one piece of information about a food 303, e.g. a food inserted in the cooking cavity of the oven 301 and subjected to cooking.

Preferably, the means 302 for obtaining at least one piece of information about at least one food comprise a visible or invisible image sensor adapted to gather information without contact. In a particular embodiment, the means 302 comprise an image sensor, such as an HD webcam. In addition, the means 302 comprise information processing means configured for deriving information about the food from the acquired images. Preferably, the information about the food 303 comprises: food typology and/or food cooking typology.

The oven 301 further comprises means of transmitting 304 the information about the food 303 to a biometric monitoring system, as will be described more in detail below.

In particular, in a preferred embodiment a radio-frequency module is installed on the oven control motherboard (not shown). The radio-frequency module is adapted to communicate, preferably via Bluetooth or WiFi protocol, with the biometric monitoring system, which gathers information about the user's physiological activity, as previously described.

Figure 4:
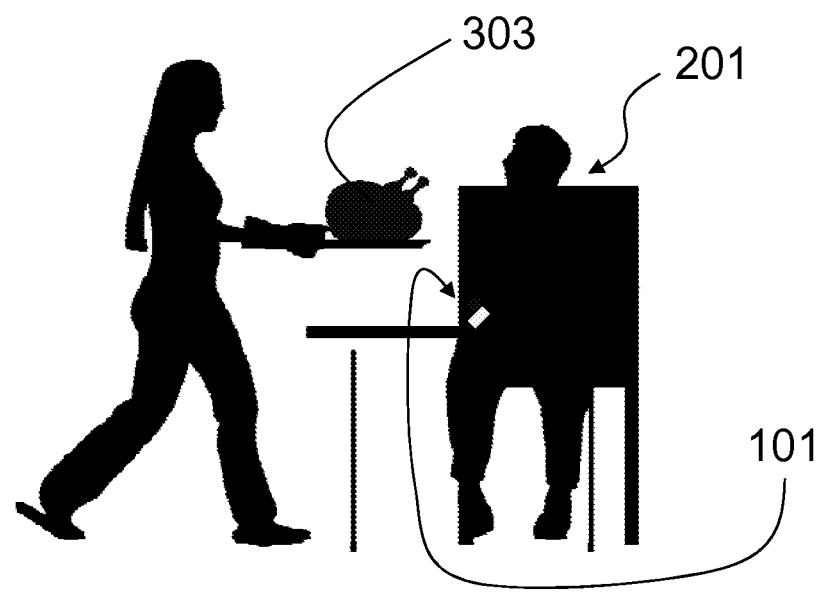
FIG. 4 shows a food coming from the household appliance of FIG. 3, being presented to a user.

FIG. 4 shows the food 303, taken from the oven 301, being presented to the user 201, who is still wearing the bracelet 101. While the user 201 is eating the food 303, the bracelet 101 keeps monitoring in real time the vital parameters of the user 201, as previously described.

Figure 5:
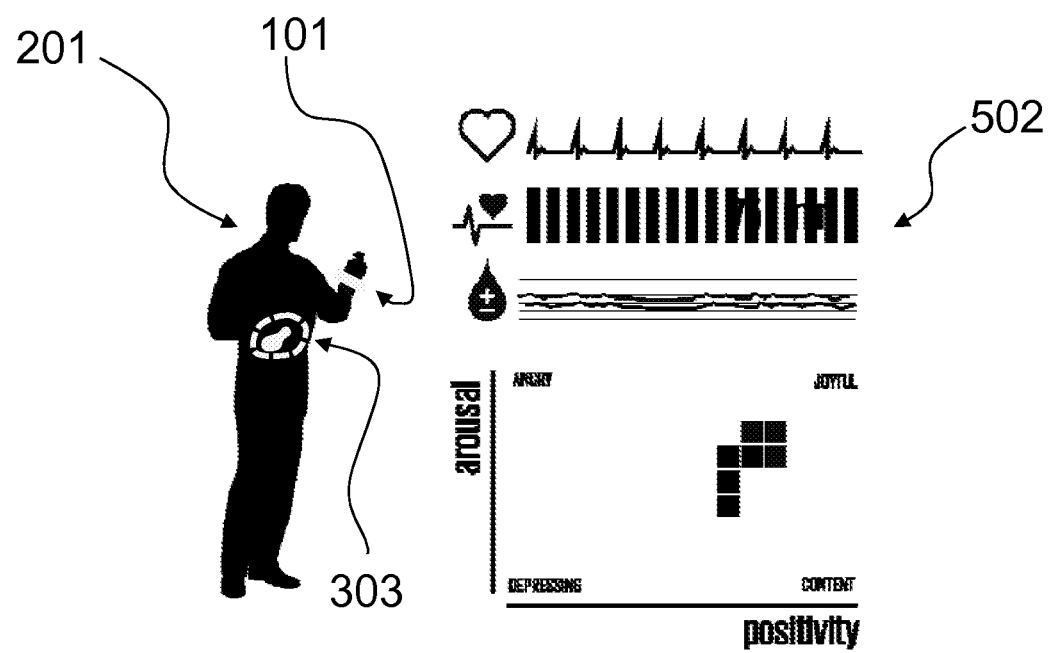
FIG. 5 shows the operation of the device of FIG. 1, worn by a user, in association with the household appliance of FIG. 3.

FIG. 5 illustrates the operation of the bracelet 101, worn by the user 201, in association with the oven 301. After the user 201 has finished his/her meal by ingesting the food 303, he/she is presented with a screen 502 that summarizes the various information about his/her vital and biometric parameters. The screen 502 is different from the screen 202, in that the user has now ingested the food 303, and therefore his/her degree of satisfaction has increased, as shown by the different configuration of the visual indicators at the bottom of the screen 502.

The information gathered by the oven 301 thus complements the information gathered by the bracelet 101, so that the user 201 can monitor the data that correlate the ingested food and his/her dietary habits to variations in the vital and biometric parameters.

In this manner, correlations can be established between the health and mood changes of the user 201, based on the consumed foods 303 and their cooking typology. The user 201 thus improves his/her awareness about what he/she eats and how the food is cooked: the user can then be given recommendations about his/her diet, his/her habits, and recipes for preparing the foods, even automatically.

Figure 6:
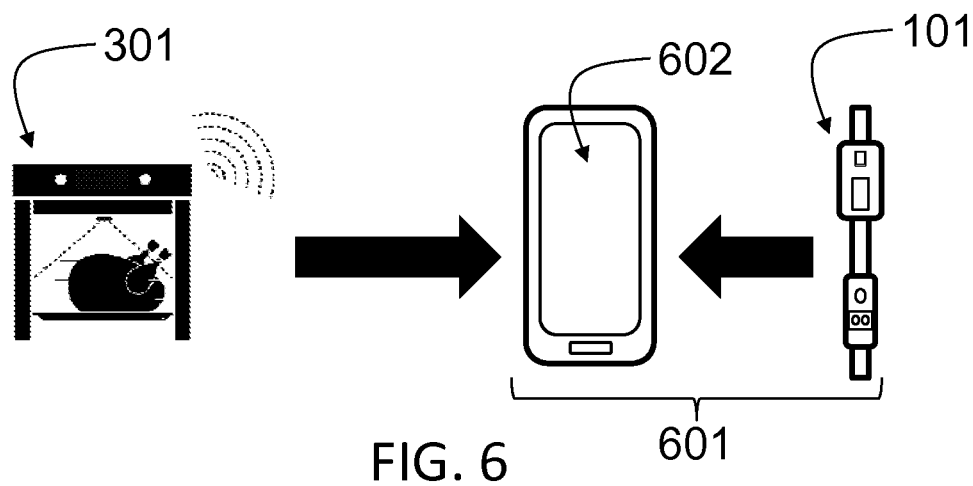
FIG. 6 shows a first embodiment of the exchange of information between a household appliance and a biometric monitoring system.

FIG. 6 illustrates a first preferred embodiment of the exchange of information between the oven 301 and the bracelet 101.

In this embodiment, the biometric monitoring system 601 comprises the bracelet 101 and additionally a processing device 602, such as a smartphone, a tablet, or a generic PC.

The oven 301 is adapted to transmit the information about the food 303 to the processing device 602; likewise, also the bracelet 101 is adapted to transmit biometric information about the user's physiological parameters to the processing device 602. The information flows are shown in the drawing by means of thick arrows.

Thus, the devices 301 and 101 send to the processing device 602 information within their competence; in turn, the processing device 602 presents the user with information exemplified in the screens 202 and 502.

Figure 7:
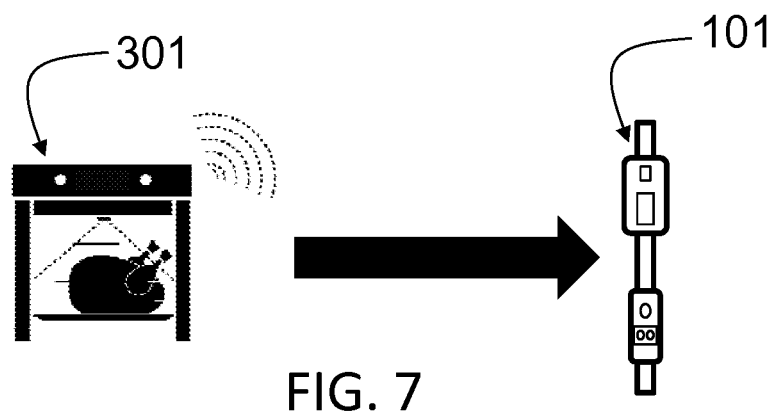
FIG. 7 shows a second embodiment of the exchange of information between a household appliance and a biometric monitoring system.

FIG. 7 illustrates a second preferred embodiment of the exchange of information between the oven 301 and the bracelet 101.

In this embodiment, the biometric monitoring system 601 only comprises the bracelet 101 wearable by the user.

The oven 301 is thus adapted to transmit the information about the food 303 directly to the bracelet 101, which already has the biometric information about the user's physiological parameters. In this case as well, the information flow is represented in the drawing by thick arrows.

In this way, the devices 301 and 101 directly cooperate with each other in order to the present user with the information exemplified by the screens 202 and 502.

Figure 8:
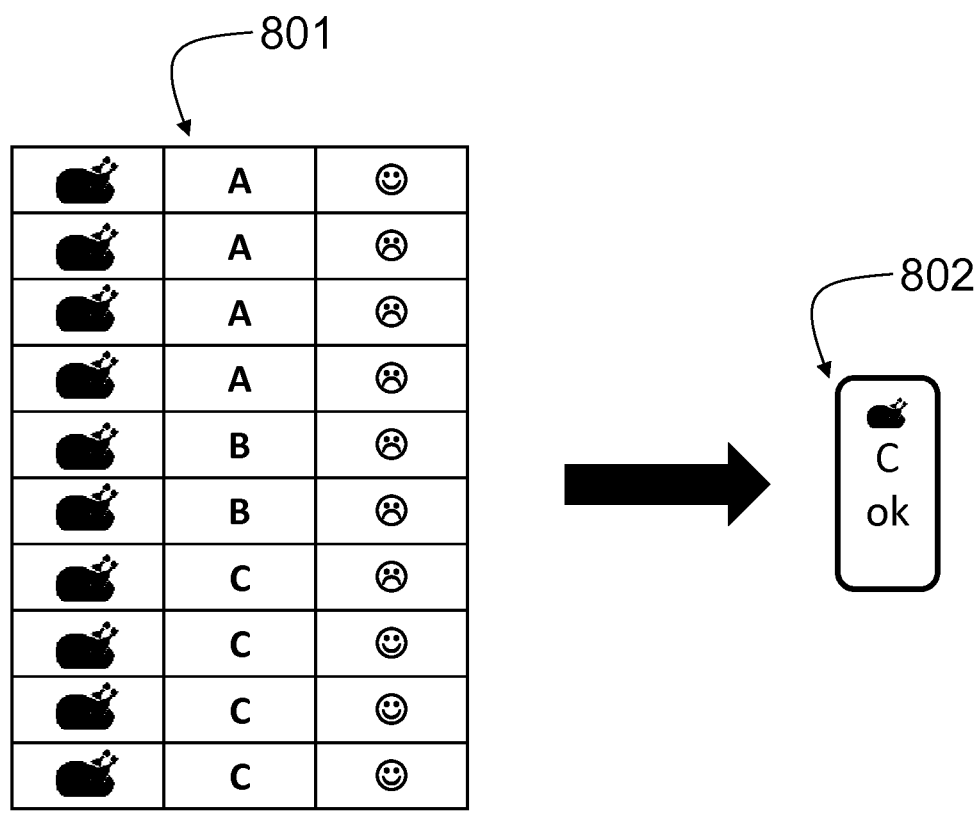
FIG. 8 shows a mode of processing the information gathered by a household appliance and by a biometric monitoring system.

FIG. 8 illustrates a preferred and advantageous mode in which the devices 301 and 101 cooperate in order to present the user with some specific information.

In particular, the oven 301 or the biometric monitoring system 101 can store a plurality of pieces of information, which are exemplified in Table 801. In particular, the information shown in Table 801 relates to: the type of food 303 prepared, the food cooking cycle, and a global parameter representative of the user's biometric conditions.

By filling the table and storing the information several times in succession, it is possible to complete a case study that combines food typology, recipe/cooking cycle and user satisfaction, and then identify the preferred or best combinations for the user.

In this example, Table 801 refers to cases in which the user has consumed the same food, i.e. "chicken", cooked according to three cooking cycles or recipes "A", "B" and "C". The user's biometric satisfaction is represented in Table 801 by a happy or unhappy face, depending on the degree of satisfaction/usefulness for the user.

In the example of Table 801 it is verified that, at the end of a series of 10 "chickens", a plurality of pieces of information have been gathered which indicate that the best cooking cycle is the cycle "C", which obtained the higher number of likes from the user.

In addition or as an alternative to the screens 502 and 202, it is therefore possible to present the user with a summary screen 802 taking into account the previously processed information, i.e. informing the user 201 that: the most suitable recipe for "chicken" is the cooking cycle "C".

It is obvious that, in the light of the teachings of the present description, the man skilled in the art may conceive further variants of the present invention, without however departing from the protection scope as defined by the appended claims.

For example, further variants may be conceived wherein the information gathered by the devices 301 and 101 can be transmitted, so long as they cooperate together in order to present the user with the biometric information exemplified herein.

Besides, the present description has been focused on a household appliance like an oven, wherein the transmitted information concerns a food subjected to cooking. Further embodiments of the present invention may however be conceived by the man skilled in the art on the basis of the teachings of the present description.

For example, the household appliance may be a refrigerator, wherein the information relates to a food being removed from the refrigerated cell.

For example, the household appliance may be a scale, wherein the information relates to a food being weighed by the scale.

For example, the household appliance may be a citrus-fruit squeezer, wherein the information relates to the type of juice being produced by the user.

For example, the household appliance may be a kitchen robot, wherein the information relates to a food being prepared.

The present invention is therefore applicable to a large number of household appliances, to which will then advantageously become interfaceable to a biometric monitoring system of a user, in accordance with the present invention.

The invention claimed is:

1. A household appliance comprising:
    an image sensor configured to acquire one or more images of at least one food interacting with the household appliance;
    a processor configured to utilize the acquired images of the least one food to derive at least one piece of information about the at least one food with which said household appliance is interacting; and
    a module configured for transmitting said at least one piece of information about the at least one food to a biometric monitoring system of a user.

2. The household appliance according to claim 1, wherein said biometric monitoring system comprises monitoring means for monitoring at least one vital parameter of the user in real time.

3. The household appliance according to claim 2, wherein said monitoring means comprise at least one of a photoplethysmograph, a thermometer, a dermal electrode, and an accelerometer.

4. The household appliance according to claim 1, wherein said at least one piece of information about the at least one food comprises at least one of a food typology and a food preparation typology.

5. The household appliance according to claim 4, wherein the food preparation typology comprises information about a preparation cycle being carried out by said household appliance.

6. The household appliance according to claim 4, wherein the image sensor is a visible or invisible image sensor and the processor is configured to gather said at least one piece of information about the at least one food without contact.

7. The household appliance according to claim 1, comprising wireless transmission means for transmitting said at least one piece of information about the at least one food via a Bluetooth protocol or a WiFi protocol.

8. The household appliance according to claim 1, wherein said biometric monitoring system comprises a device wearable by said user.

9. The household appliance according to claim 8, wherein said household appliance is configured to transmit said at least one piece of information about the at least one food directly to said device wearable by said user.

10. The household appliance according to claim 8, wherein said biometric monitoring system further comprises a processing device, wherein said household appliance is configured to transmit said at least one piece of information about the at least one food to said processing device, and wherein said device wearable by said user is configured to transmit biometric information to said processing device.

11. The household appliance according to claim 1, wherein said household appliance comprises an oven, and said at least one piece of information about the at least one food relates to a food being cooked in said oven.

12. The household appliance according to claim 1, wherein a display of the biometric monitoring system displays selected data based on utilizing the at least one piece of information about the at least one food in conjunction with particular information associated with vital information regarding at least one vital parameter of the user.

13. The household appliance according to claim 1, wherein said biometric monitoring system of the user is configured to store at least one piece of information about the at least one food.

\* \* \* \* \*

UNITED STATES PATENT AND TRADEMARK OFFICE
CERTIFICATE OF CORRECTION

PATENT NO. : 9,687,150 B2
APPLICATION NO. : 14/677100
DATED : June 27, 2017
INVENTOR(S) : Filippo Matarazzi et al.

It is certified that error appears in the above-identified patent and that said Letters Patent is hereby corrected as shown below:

In the Specification

Column 6, Line 5 reads:
number of household appliances, to which will then advan-
Should read:
number of household appliances, which will then advan- Signed and Sealed this
Thirteenth Day of March, 2018

Andrei Iancu
*Director of the United States Patent and Trademark Office*